US012694971B2

(12) United States Patent
Chaudhury et al.

(10) Patent No.: US 12,694,971 B2
(45) Date of Patent: Jul. 28, 2026

(54) AUTONOMOUS IMAGE ACQUISITION START-STOP MANAGING SYSTEM

(71) Applicant: KONINKLIJKE PHILIPS N.V., Eindhoven (NL)

(72) Inventors: Sudipta Chaudhury, Bangalore (IN); Rajendra Singh Sisodia, Bhopal (IN); Gereon Vogtmeier, Aachen (DE); Christopher Leussler, Hamburg (DE); Sarif Naik, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 133 days.

(21) Appl. No.: 18/566,122

(22) PCT Filed: May 18, 2022

(86) PCT No.: PCT/EP2022/063394
    § 371 (c)(1),
    (2) Date: Dec. 1, 2023

(87) PCT Pub. No.: WO2022/253570
    PCT Pub. Date: Dec. 8, 2022

(65) Prior Publication Data
    US 2024/0257945 A1 Aug. 1, 2024

(30) Foreign Application Priority Data
    Jun. 4, 2021 (EP) .................................... 21177678

(51) Int. Cl.
    *G16H 30/20* (2018.01)
    *A61B 6/00* (2006.01)

(52) U.S. Cl.
    CPC .............. *G16H 30/20* (2018.01); *A61B 6/545* (2013.01); *A61B 6/548* (2013.01); *A61B 6/563* (2013.01)

(58) Field of Classification Search
    CPC ........ G16H 30/20; G16H 40/63; G16H 40/67; G16H 40/20; A61B 6/545; A61B 6/548;
    (Continued)

(56) References Cited

U.S. PATENT DOCUMENTS

| | | | |
|---|---|---|---|
| 6,674,449 B1 * | 1/2004 | Banks .................. | A61B 5/7435 715/740 |
| 10,540,731 B2 * | 1/2020 | Hernandez ............. | G06Q 10/06 |

(Continued)

FOREIGN PATENT DOCUMENTS

WO     WO-2014026958 A1 *     2/2014     ............. G16H 30/20

OTHER PUBLICATIONS

Oberweis Andreas: "Person-to-Application Processes: Workflow Management : Bridging People and Software through Process Technology" In: "Process-Aware Information Systems : Bridging People and Software through Process Technology", Sep. 2, 2005 (Sep. 2, 2005), John Wiley & Sons, Inc., Hoboken, NJ, USA, XP55953068.

(Continued)

*Primary Examiner* — Jason S Tiedeman

(57) ABSTRACT

The present invention relates to autonomous imaging. A system and method is proposed that automatically evaluates the readiness index of an autonomous scan procedure and continuously evaluates whether to continue, pause, or about the imaging procedure.

17 Claims, 6 Drawing Sheets

(58) Field of Classification Search
CPC ......... A61B 6/563; A61B 6/586; A61B 5/055; A61B 6/032; A61B 6/037
USPC ........................................................ 705/2, 3
See application file for complete search history.

(56) References Cited

U.S. PATENT DOCUMENTS

| | | | | |
|---|---|---|---|---|
| 2005/0285745 | A1* | 12/2005 | Heck | G16H 20/40 |
| | | | | 340/506 |
| 2009/0150184 | A1 | 6/2009 | Spahn | |
| 2012/0221728 | A1* | 8/2012 | Dubbels | G16H 30/40 |
| | | | | 709/226 |
| 2013/0225950 | A1 | 8/2013 | Van Elswijk et al. | |
| 2014/0088405 | A1 | 3/2014 | Assmann et al. | |
| 2016/0000383 | A1 | 1/2016 | Lee et al. | |
| 2016/0081659 | A1* | 3/2016 | Perrey | A61B 8/463 |
| | | | | 600/437 |
| 2019/0013092 | A1 | 1/2019 | Van Halteren et al. | |
| 2019/0148011 | A1 | 5/2019 | Rao et al. | |
| 2019/0228857 | A1* | 7/2019 | Lin | G06N 20/00 |
| 2020/0160574 | A1* | 5/2020 | Nye | A61B 5/7435 |
| 2020/0205748 | A1 | 7/2020 | Pautsch et al. | |
| 2021/0127976 | A1* | 5/2021 | Starobinets | A61B 5/7475 |
| 2021/0241137 | A1* | 8/2021 | Jain | G16H 10/20 |
| 2021/0345993 | A1* | 11/2021 | Dickie | A61B 8/0866 |
| 2022/0068472 | A1* | 3/2022 | Arroyo Camejo | G16H 15/00 |

OTHER PUBLICATIONS

Anonymous: "Workflow management system—Wikipedia", Jun. 1, 2021.

International Search Report and Written Opinion from PCT/EP2022/063394 mailed Aug. 30, 2022.

* cited by examiner

AUTONOMOUS IMAGE ACQUISITION START-STOP MANAGING SYSTEM

CROSS REFERENCE TO RELATED APPLICATIONS

This application is a U.S. national phase application of International Application No. PCT/EP2022/063394 filed on May 18, 2022, which claims the benefit of EP Application Serial No. 21177678.6 filed on Jun. 4, 2021 and is incorporated herein by reference.

FIELD OF THE INVENTION

The present invention relates to autonomous imaging. In particular, the present invention relates to a rule engine apparatus and a method for evaluating an autonomous scan procedure for controlling an autonomous imaging apparatus to acquire an image of a patient, an autonomous imaging system, a computer program product, and a computer readable medium.

BACKGROUND OF THE INVENTION

High patient throughput is crucial for many medical imaging facilities. Moreover, imaging will become more and more autonomous in future with less operator-dependent actions and automated workflow steps, for increasing the throughput while reducing the operational costs.

SUMMARY OF THE INVENTION

It is thus an object of the present invention to provide an improved autonomous imaging system and method.

The object of the present invention is solved by the subject-matter of the independent claims. Further embodiments and advantages of the invention are incorporated in the dependent claims. Furthermore, it shall be noted that all embodiments of the present invention concerning a method might be carried out with the order of the steps as described, nevertheless this has not to be the only and essential order of the steps of the method as presented herein. The method disclosed herein can be carried out with another order of the disclosed steps without departing from the respective method embodiment, unless explicitly mentioned to the contrary hereinafter.

According to a first aspect of the present invention, there is provided a rule engine apparatus for evaluating an autonomous scan procedure for controlling an autonomous imaging apparatus to acquire an image of a patient. The rule engine apparatus comprises an input unit, a master rule engine unit, a plurality of workflow step rule engine units, each workflow step rule engine unit being associated with a respective set of rules, and an output unit. The input unit is configured to receive a data input indicative of an event in an autonomous image acquisition workflow. The master rule engine unit is configured to select, for the data input, one or more workflow step rule engine units from the plurality of workflow step rule engine units to determine a set of readiness indices, wherein each of the one or more selected workflow step rule engine units is configured to execute, in response to the data input, one or more rules of the respective rule set to generate a respective readiness index indicative of a state of being prepared for a particular step in the autonomous image acquisition workflow. The master rule engine unit is further configured to determine an action of the autonomous imaging apparatus based on the set of readiness indices. The output unit is configured to output the determined action, which is usable for controlling the autonomous imaging apparatus.

The inventors of the present invention have found out that in an autonomous imaging system, a defined methodology should be in place to start, stop, or abort the imaging procedure. Criteria such as suitability of patient for autonomous scan, subsequent preparations, prevention of injury, and subjective human intervention are even more rigorously need to avoid any untoward situations. The inventors of the present invention have also found out that a well-defined procedure may be required in autonomous imaging system to put in place to cover any foreseen eventuality and some unforeseen ones.

To this end, a rule engine apparatus is proposed for evaluating an autonomous scan procedure for controlling an autonomous imaging apparatus to acquire an image of a patient. The proposed rule engine apparatus is implemented as "systems of self-contained systems" with each self-contained system can have its own "workflow step rule engine unit" and a master rule engine unit whose output may be states indicative of an action to be performed by the autonomous imaging apparatus, such as "start", "stop", and "abort". The proposed rule engine apparatus the ability to process input data in autonomous medical workflow settings and to decide on specific workflow steps readiness as well as readiness at the autonomous scan level.

Each self-contained system collects data from various data sources. For example, the data can be sourced from relevant sensors such as spirometer, camera based detection mechanism, Augmented Reality (AR), Virtual Reality (VR), physiological data sensor (e.g. Spo2 sensor, plethysmography sensor, etc.), clinical data (lung capacity, earlier incident of any lung/heart disease, etc.), patient profile (athletic/ swimmer), etc. The data may be sourced from data (e.g. image data) collected from the environment in the imaging room. The data may be sourced from machine setting data (e.g. scan protocol). These data sources may be processed by different processing steps and finally fed as a data input for one or more rules.

Each workflow step rule engine for real-time data processing is a kind of decision engine that evaluates the data input according to a set of defined rule-rules and determines an a readiness index. The readiness index may be a probability number between 0 and 1 or may be discrete states, such as "low", "medium", and "high". Since each of the rule system, rules, processing steps are self-contained, the readiness index may be tailored based on e.g. risk factors, impact, and the like in the master rule engine unit.

The evaluation step of each self-contained system is a readiness index. The master rule engine takes these readiness indices evaluates the autonomous image acquisition workflow and outputs an action to be performed by the autonomous imaging apparatus, such as start, abort, stop the imaging procedure, or human intervention.

The proposed rule engine apparatus may also help drive clinical and operational efficiency across all phases of the image acquisition, from patient preparation to image quality assessment. The proposed rule engine apparatus may help reduce variability and staff workload, increase productivity, and increase patient throughput. Further, criteria, such as suitability of patient for autonomous scan, subsequent preparations, prevention of injury, subjective human intervention, and the like are reflected in the readiness indices, which are fed as an input to the master rule engine unit to make a decision. Therefore, untoward situations may be avoided.

According to an embodiment of the present invention, each rule corresponds to a specific workflow step in the autonomous image acquisition workflow, and workflow steps between different rules are different.

According to an embodiment of the present invention, the master rule engine unit is configured to associate the data input to at least one of the one or more selected workflow step rule engine units with a sub-step of the specific workflow step.

For example, the patient preparation workflow step may comprise different multiple processing steps including, but not limited to, breath holding, following instructions, anxiety level, etc. Each processing step may also be referred to as a sub-step of the corresponding workflow step.

According to an embodiment of the present invention, the data input comprises an output from a pre-trained machine-learning algorithm.

In other words, some data inputs may be pre-processed by a pre-trained machine-learning algorithm to determine the probability of whether an event is likely to happen. The predictions from the machine-learning algorithm are then an input into the rules. The rules then evaluate the output of the machine-learning model and provide an output value.

The machine-learning algorithm may be a neural network, a support vector machine, a decision tree, or the like. For training the machine-learning algorithm, workflow details from previous imaging examinations may be used.

The machine-learning algorithm may optimize some kind of process, which cannot be fully enumerated with a deterministic set of rules.

According to an embodiment of the present invention, the plurality of workflow step rule engine units are configured to use an active learning mechanism to update respective rule sets.

The process of performing a scan is very dynamic and it may be difficult to determine all conditions on which a system should abort and restart. The system and condition under which the events happened may be learned during every scan of the device starting from patient preparing to scan complete. An active learning mechanism may be put in place, which captures each state of the machine and corresponding conditions of the machine during each event. In this process, each state of the machine may be tagged with the event. Any new state in which an abort action occurred may be a new rule for the system of systems. This will be explained in detail with respect to the example shown in FIG. 3.

According to an embodiment of the present invention, the data input comprises one or more of: data collected from the patient, data collected from a device used in the autonomous scan procedure, data collected from the autonomous imaging apparatus, data collected from an imaging room, and data collected from a user input.

The data input may be used to evaluate e.g. suitability of patient for an autonomous scan, subsequent preparations, prevention of injury, subjective human interventions, etc.

For example, data collected from the patient may include e.g. sensor data, clinical data, and patient profile data.

For example, data collected from a device used in the autonomous scan procedure may include data indicative of status and/or functionality of a device, such as electrical coil, sensors, and the like.

For example, data collected from the autonomous imaging apparatus may include data indicative of scan protocol, working status of the imaging apparatus, and the like.

For example, data collected from the imaging room may include image data of the imaging room, which may be used to detect whether a foreign object closed to the imaging system may interfere the imaging procedure.

According to an embodiment of the present invention, the data collected from the patient comprises one or more of: sensor data collected from sensors for monitoring the patient, clinical data of the patient, and patient profile data.

According to an embodiment of the present invention, the determined action comprises at least one of: starting image acquisition, aborting image acquisition, and stopping image acquisition.

According to an embodiment of the present invention, for determining the action of starting image acquisition, the master rule engine unit is configured to select, for the data input, one or more workflow step rule engine units from the plurality of workflow step rule engine units to determine a set of readiness indices about a device indicative a state of the autonomous imaging apparatus being prepared for starting image acquisition and a set of readiness indices about the patient indicative a state of the patient being prepared for starting image acquisition.

According to an embodiment of the present invention, for determining the action of aborting image acquisition, the master rule engine unit is configured to select, for the data input, one or more workflow step rule engine units from the plurality of workflow step rule engine units to determine a set of readiness indices about a device indicative a state of the autonomous imaging apparatus not being suitable for continuing image acquisition and/or a set of readiness indices about the patient indicative a state of the patient not being suitable for continuing image acquisition.

According to an embodiment of the present invention, for determining the action of stopping image acquisition, the master rule engine unit is configured to select, for the data input, one or more workflow step rule engine units from the plurality of workflow step rule engine units to determine a set of readiness indices indicative of one or more of the following: planned end, scan protocol completed, image quality assessment, coverage of organ of interest, and stable internet access by remote operator.

According to a second aspect of the present invention, there is provided an autonomous imaging system, comprising an autonomous imaging apparatus and a rule engine apparatus according to the first aspect and any associated example. The autonomous imaging apparatus is configured to acquire an image of a patient based on a determined action provided by the rule engine apparatus.

Examples of the autonomous imaging apparatus may include, but are not limited to, x-ray imaging apparatus, magnetic resonance imaging apparatus, computerized tomography scanner, positron emission tomography scanner, and the like.

According to a third aspect of the present invention, there is provided a method for evaluating an autonomous scan procedure for controlling an autonomous imaging apparatus to acquire an image of a patient, comprising:

a) receiving, by an input unit, a data input indicative of an event in an autonomous image acquisition workflow;
  b) selecting, by a master engine unit, for the data input, one or more workflow step rule engine units from a plurality of workflow step rule engine units to determine a set of readiness indices, wherein each workflow step rule engine unit is associated with a respective set of rules; and
    wherein each of the one or more selected workflow step rule engine units is configured to execute, in response to the data input, one or more rules of the respective rule set to generate a respective readiness index indicative of a state of being prepared for a particular step in the autonomous image acquisition workflow:

c) determining, by the master engine unit, an action of the autonomous imaging apparatus based on the set of readiness indices; and d) outputting, by an output unit, the determined action, which is usable for controlling the autonomous imaging apparatus.

According to a fourth aspect of the present invention, there is provided a computer program product comprising instructions which, when executed by at least one processing unit, cause the at least one processing unit to perform the steps of the method according to the third aspect and any associated example.

According to a fifth aspect of the present invention, there is provided a computer readable medium having stored the program product.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1:
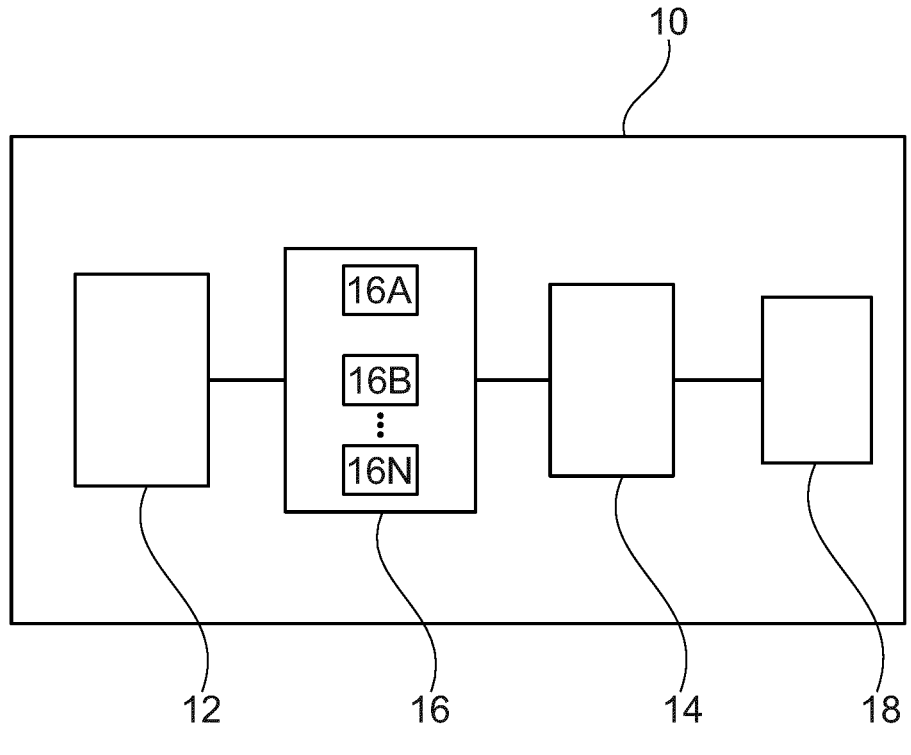
FIG. 1 shows an exemplary rule engine apparatus 10 for evaluating an autonomous scan procedure for controlling an autonomous imaging apparatus to acquire an image of a patient.

FIG. 1 shows an exemplary rule engine apparatus 10 for evaluating an autonomous scan procedure for controlling an autonomous imaging apparatus to acquire an image of a patient. The rule engine apparatus 10 may be any computing device, including desktop and laptop computers, smartphones, tablets, etc. The rule engine apparatus 10 may be a general-purpose device or a device with a dedicated unit of equipment suitable for providing the below-described functionality. In the example of FIG. 1, the components of the rule engine apparatus 10 are shown as integrated in one single unit. However, in alternative examples (not shown), some or all components may be arranged as separate modules in a distributed architecture and connected in a suitable communication network, such as a 3rd Generation Partnership Project (3GPP) network, a Long Term Evolution (LTE) network, Internet, LAN (Local Area Network), Wireless LAN (Local Area Network), WAN (Wide Area Network), and the like. The rule engine apparatus 10 and its components may be arranged as dedicated FPGAs or as hardwired standalone chips. In some examples, the rule engine apparatus 10 or some of its components may be resident in a console running as software routines.

The rule engine apparatus 10 comprises an input unit 12, a master rule engine unit 14, a plurality of workflow step rule engine units 16, and an output unit 18. In the example shown in FIG. 1, the plurality of workflow step rule engine units 16 comprises workflow step rule engine units 16A to 16N. Each unit may be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

The input unit 12 is configured to receive a data input indicative of an event in an autonomous image acquisition workflow. The input unit 12 is, in an example, implemented as an Ethernet interface, a USB™ interface, a wireless interface such as a WiFi™ or Bluetooth™ or any comparable data transfer interface enabling data transfer between input peripherals and the processing unit 14.

The event may be any event that may have an influence on the autonomous imaging procedure, which may cause the imaging process to start, abort, or stop. Examples of the events may include events that have an influence on e.g. suitability of patient for autonomous scan, subsequent preparations, prevention of injury, subjective human intervention, etc.

In an example, vital signs (e.g. oxygen saturation, heart rate, and systolic, and diastolic blood pressure) may be used to assess the patient's anxiety and the suitability of the patient for the autonomous scan. If it is determined that the patient has a high anxiety and high fear index, the autonomous imaging procedure may be aborted or stopped. In this example, the event is that the patient has a lot of anxiety, which has an influence on the autonomous imaging procedure.

In an example, a video signal from a video camera or a depth camera monitoring the face expression or the skin of the patient may be used to assess a pain level experienced by the patient. If the patient is experiencing a high level of pain, the autonomous imaging procedure may be aborted in order to prevent or reduce the severity of bodily injuries. In this example, the event is that the patient suffers a lot of pain, which has an influence on the autonomous imaging procedure.

Thus, the data input may comprise any data that is suitable for indicating that an event is happening or is likely to happen.

For example, the data input may comprise data collected from the patient.

In some examples, the data collected from the patient may comprise sensor data collected from one or more sensors configured to measure the patient's reaction prior to and during an autonomous imaging procedure. The sensors may be used to measure e.g. patient motion, patient pain, nervousness, etc. In an example, the sensor data may be collected from one or more physiological data sensors, which record waveforms and provide periodic measurements of vital signs such as heart rate (HR), respiratory rate (RR), peripheral arterial oxygen saturation (SpO2), arterial blood pressure (ABP), and temperature (T). In another example, the sensor data may be collected from a camera-based detection mechanism, which may be used to detect the movement of the patient. In a further example, the sensor data may be collected from three-dimensional radar sensors, which are used to monitor movement patterns of patients, persons, and devices. Radar array sensors have the advantage of creating three-dimensional point-cloud images suitable for recognition of body posture and motion, but do not allow face recognition. Radar array sensors also have the advantage of working in all lighting conditions and of not being distracted by clothing or other non-conductive objects. For example, radar arrays can detect arm or leg prostheses even when covered by clothes. Radar array sensors should ideally be set up in a way that they can monitor the patient and imaging room without requiring additional action.

In some examples, the data collected from the patient may further comprise clinical data of the patient, such as lung capacity, earlier incident of any lung or heat disease, and the like. Likewise, the patient profile (such as athletic or swimmer) may also be included in the data input. The clinical data and the patient profile may be received from a hospital database.

In some examples, the data input may comprise data collected from devices and systems. For example, the data input may comprise machine-setting data of an autonomous imaging apparatus. For example, the machine setting data may include the scan protocol, the working state of a medical equipment, etc.

In some examples, the data input may comprise data collected from the imaging room. For example, image data may be used to detect whether a foreign object closed to the imaging system may interfere the imaging procedure.

In some examples, the data input may comprise data collected from a user input, which allows subjective human intervention e.g. in case of medical emergency.

In some examples, the data input may comprise an output from a pre-trained machine-learning algorithm. In other words, some data inputs may be pre-processed by a pre-trained machine-learning algorithm to determine the probability of whether an event is likely to happen. The predictions from the machine-learning algorithm are then an input into the rules. The rules then evaluate the output of the machine-learning model and provide an output value. The machine-learning algorithm may optimize some kind of process, which cannot be fully enumerated with a deterministic set of rules. For example, one machine-learning algorithm may be used to correlate face expression in the image data with an anxiety level. In this example, instead of directly feeding the image data as a data input for one or more rules, the image data is firstly pre-processed by a machine-learning algorithm and the output of the machine-learning algorithm, i.e. the determined anxiety level, is provided for the one or more rules. The machine-learning algorithm may be a neural network, a support vector machine, a decision tree, or the like. For training the machine-learning algorithm, workflow details from previous imaging examinations may be used.

The master rule engine unit 14 is configured to select, for the data input, one or more workflow step rule engine units from the plurality of workflow step rule engine units 16 to determine a set of readiness indices. Each of the selected one or more selected workflow step rule engine units 16 is configured to execute, in response to the data input, one or more rules 20 of the respective rule set to generate a respective readiness index indicative of a state of being prepared for a particular step in the autonomous image acquisition workflow.

In other words, the proposed rule engine apparatus 10 is implemented as "systems of self-contained systems" with each self-contained system can have its own "workflow step rule engine unit" and a master rule engine unit whose output may be states indicative of an action to be performed by the autonomous imaging apparatus, such as "start", "stop", and "abort". The state "re-start" may be similar to the state "start".

Figure 2:
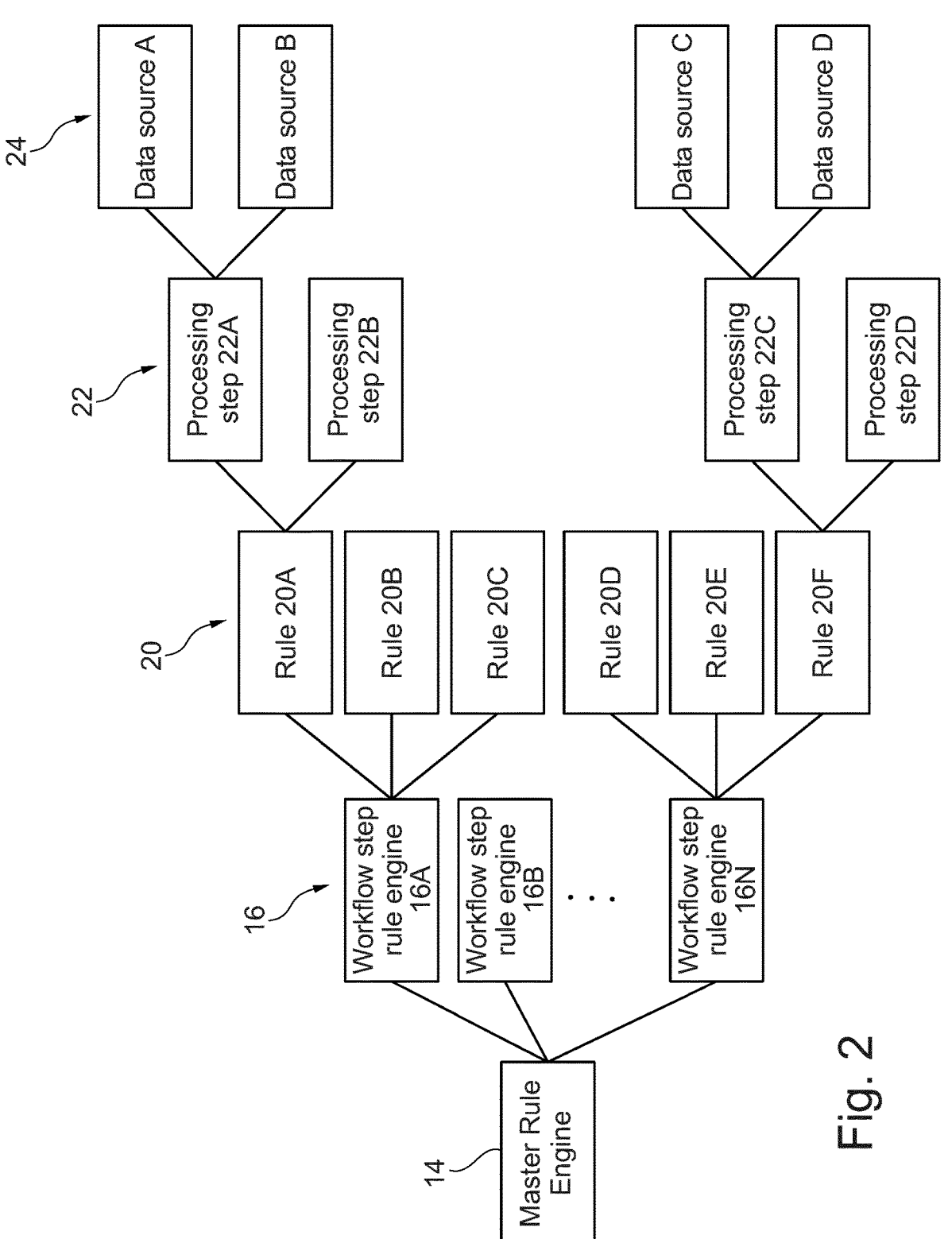
FIG. 2 shows a schematic block diagram illustrating an overall rule engine flow.

FIG. 2 shows a schematic block diagram illustrating an overall rule engine flow. As shown in FIG. 2, each self-contained system comprises a workflow step rule engine unit 16 and a self-contained system of rules 20. Each self-contained system works on defined rules for a specific segment of an autonomous image acquisition workflow. In other words, each workflow step rule engine 16 for real-time data processing is a kind of decision engine that evaluates the data input according to a set of defined rule and determines an output value.

For example, the workflow step rule engine 16A receives the data input from one or more data sources 24, such as data sources A and B shown in FIG. 2. The data input may comprise data collected from the patient, devices, system, the imaging room, and/or the user input as discussed above.

The master rule engine unit 14 is configured to select, for the data input, one or more workflow step rule engine units 16 from the plurality of workflow step rule engine units 16, such as units 16A-16N shown in FIG. 2, to determine a set of readiness indices. As shown in FIG. 2, one or more rules 20 may involve multiple processing steps. For example, the patient preparation workflow step may comprise different multiple processing steps including, but not limited to, breath holding, following instructions, anxiety level, etc. Each processing step may also be referred to as a sub-step of the corresponding workflow step.

The evaluation step of each self-contained system is a readiness index. Each workflow step rule engine unit 16 may evaluate data from various sources and provide a readiness index. As discussed above, some rules may involve multiple processing steps. For example, rule 20A comprises processing steps 22A and 22B. For example, in the above-mentioned patient preparation workflow steps, one of the readiness indices may be "patient readiness index", which is focused on whether the patient is ready for the scan in autonomous settings. This index may have different readiness indices and corresponding rules engine setup. Exemplary readiness indices may include, but are not limited to, "breath hold readiness index", "instruction following index", "anxiety index", and "Metal object risk index".

Some readiness indices may be a probability number between 0 and 1. Some readiness indices may be discrete states, such as "low", "medium", and "high".

Turning back to FIG. 1, the master rule engine unit 14 takes all these readiness indices to evaluate the autonomous image acquisition workflow and output an action to be performed by the autonomous imaging apparatus via the output unit 18 as mentioned above. The determined action is usable for controlling the autonomous imaging apparatus.

The output unit 18 is, in an example, implemented as an Ethernet interface, a USB™ interface, a wireless interface such as a WiFi™ or Bluetooth™ or any comparable data transfer interface enabling data transfer between output peripherals and the processing unit 14.

Figure 3:
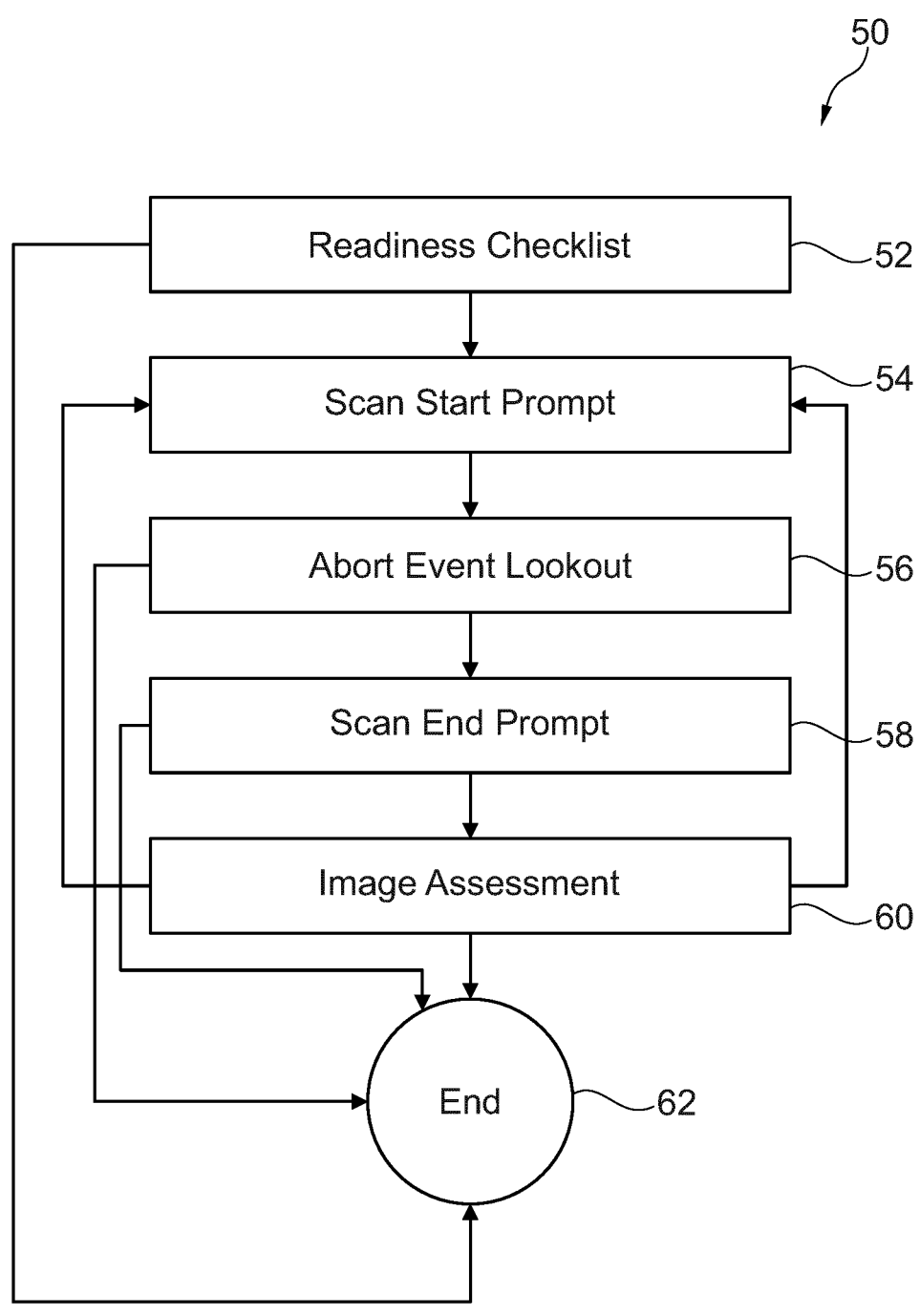
FIG. 3 shows a schematic block diagram illustrating an exemplary overall workflow.

FIG. 3 shows a schematic block diagram illustrating an exemplary overall workflow 50. For purposes of illustration, the exemplary autonomous image acquisition workflow is broadly classified into six specified workflow steps: readiness checklist, scan start prompt, abort event lookout, scan end prompt, image assessment, and end.

In the first workflow step 52, i.e. readiness checklist, one or more workflow step rule engine units may be provided to evaluate data from one or multiple data sources and to provide one or more readiness indices, such as a patient readiness index indicative of the readiness of the patient for the scan in autonomous settings and a device readiness index indicative of the readiness of the system for the scan in autonomous settings.

In this workflow step, the data input may comprise data collected from the patient. In some examples, the data may comprise sensor data obtained from one or more sensors that measure the patient's reaction. For example, the sensor data may comprise image data obtained from monitoring the patient movement before the scan procedure and vital signs obtained from monitoring the patient's anxiety level before the scan procedure. In some examples, if a contrast material is needed for the imaging procedure, the data input may further comprise data indicative of whether the contrast material has been injected. In some examples, if anesthesia or sedatives are needed for the imaging procedure, the data input may further comprise data indicative if whether the anesthesia or sedatives have been given to the patient. Further, the data input may comprise identification of the patient, data indicative of whether there is any metal objects in the body, and pre-existing conditions like pregnancy, allergy, medication, and the like, which may be collected from a hospital database. These data inputs may be used to determine whether the patient is ready for starting the scan. Thus, multiple workflow step rule engine units 16 may be used to provide different readiness indices, such as "anxiety index", "sedation index", "contrast material index", "metal object risk index", and "patient condition risk index".

In some examples, the data input may comprise data collected from devices and systems. For example, the data input may comprise data indicative of scan protocol selection, data indicative of coil selection, data indicative of working status of a medical equipment, data indicative of disinfection of device performed, data indicative of stress-test of remote VPN connection to remote operator, data indicative of status and positioning of a camera system, data indicative of balance in patient support, and data indicative of cardiac gating probe placement. These data inputs may be used to determine whether devices and systems are well prepared for starting the scan. Thus, multiple workflow step rule engine units 16 may be used to provide different readiness indices, such as "coil readiness index", "scan protocol readiness index", "medical equipment readiness index", "camera system readiness index", "VPN connection readiness index", "patient support readiness index", and "cardiac gating probe placement readiness index".

In some examples, the data input may comprise user input data, such as patient confirmation, obtained via a user interface. Examples of user interfaces that may be employed in various implementations of the present disclosure include, but are not limited to, switches, potentiometers, buttons, dials, sliders, track balls, display screens, various types of graphical user interfaces (GUIs), touch screens, microphones, cameras and other types of sensors that may receive some form of human-generated stimulus and generate a signal in response thereto. The user input data thus allows subjective human intervention.

In some examples, the data input may comprise data collected from one or more sensors that monitor the environment in the scanner room. The sensor data may comprise video signals from a video camera that monitors e.g. devices present in the scanner room, which may generate noise or image artifacts and whether the door of the scanner room is closed. These data inputs allow the system to determine whether the environment in the scanner room is suitable for the start condition. Thus, multiple workflow step rule engine units may be used to provide different readiness indices, such as "object risk index" and "scanner room readiness index".

The master rule engine unit 14 then takes the above-mentioned exemplary readiness indices in order to evaluate the autonomous image acquisition workflow and determines whether to start the scan (block 54).

Once the imaging procedure starts, one or more workflow step rule engine units 16 associated with the workflow step "Abort Event Lookout" evaluate data inputs and determine, based on these data inputs, whether an overriding emergency mechanism is required (block 56).

In some examples, the data input may comprise data collected from the patient. For examples, the data may comprise sensor data obtained from one or more sensors that measure the patient's reaction. The sensor data may comprise image data obtained from monitoring the patient movement, vital signs obtained from monitoring the patient anxiety and medical emergency, data obtained from sedation monitoring devices for monitoring premature wakeup from sedation, and/or data obtained from monitoring a pain level that is experienced by the patient. In some examples, video feeds having a field of view that covers the body part of interest received from a combination of various three-dimensional contactless motion scanner using e.g. light detection and ranging (LIDAR), radio detection and ranging (RADAR), and camera based sensor at different position may be used to measure one or more of patient motion, patient pain, and nervousness. Thus, multiple workflow step rule engine units may be used to provide different readiness indices, such as "pain index", "anxiety index", "sedation index", and "medical emergency index". For each readiness index, a threshold level may be set to determine if it is necessary to abort the scan procedure.

In some examples, the data input may comprise user input data obtained via a user interface, e.g. via an integrated emergency button integrated with an MRI scanner or a command received from a remote operator to abort the scan procedure. The user input data thus allows subjective human intervention. For example, the patient may press the integrated emergency button in case of pain and anxiety. Thus, multiple workflow step rule engine units 16 may be used to provide different readiness indices, such as "patient intervention index" and "operator intervention index".

In some examples, the data input may comprise data collected from various devices and systems. For example, the data input may comprise data indicative of electrical coil status, position of sensors, position of a mattress in the imaging system, and/or the status of internet connection to remote client. The data input thus allows the system to determine whether the status and functionality of e.g. imaging devices, systems, and internet connect are good enough to continue the autonomous imaging procedure. Thus, multiple workflow step rule engine units may be used to provide different readiness indices, such as "electrical coil status index", "sensor position index", "mattress position index", and "internet connection index".

In some examples, the data input may comprise data collected from one or more sensors that monitor the environment in the scanner room. The sensor data may comprise video signals from a video camera that monitors objects brought in the scanner room or close to the scanner during imaging and/or patient's relatives in the scanner room. These data inputs allow the system to detect whether an object and/or a person may interfere the scanning process. Thus, one or more workflow step rule engine units 16 may provide different readiness indices, such as "object interference index" and "person interference index".

The above-described exemplary readiness indices are then provided to the master rule engine unit 14 to determine whether to abort the imaging procedure.

If the imaging procedure is not aborted, one or more workflow step rule engine units associated with the workflow step "Scan End Prompt" evaluate data input and determine, based on these data inputs, whether to stop the imaging procedure (step 58). The data input may comprise data indicative of a planned end, data indicative of scan procedure completed, data indicative a coverage of organ of interest, and data indicative of stable internet access by remote operator. Thus, multiple workflow step rule engine units may provide different readiness indices, such as "planned end index", "scan procedure completeness index", "organ coverage index", and "internet connection index".

Once the imaging procedure stops, one or more workflow step rule engine units associated with the workflow step "Image Assessment" evaluate image data and determine, based on these data inputs, whether it is necessary to perform another scan (step 60).

If the image quality meets predefined criteria, the autonomous imaging procedure ends (step 62).

It will be appreciated that since each of the rule engine system, rules, and processing steps are self-contained, the above-discussed exemplary readiness indices may be tailored individually based on e.g. risk factors and impact in the master rule engine unit.

The process of performing a scan is very dynamic and it may be difficult to determine all conditions on which a system should abort and restart. The system and condition under which an event happened may be learned during every scan of the device starting from patient preparing to scan complete. An active learning mechanism may be put in place, which captures each state of the machine and corresponding conditions of the machine during each event. In this process, each state of the machine may be tagged with the event. Any new state in which an abort action occurred may be a new rule for the system of systems.

Figure 4:
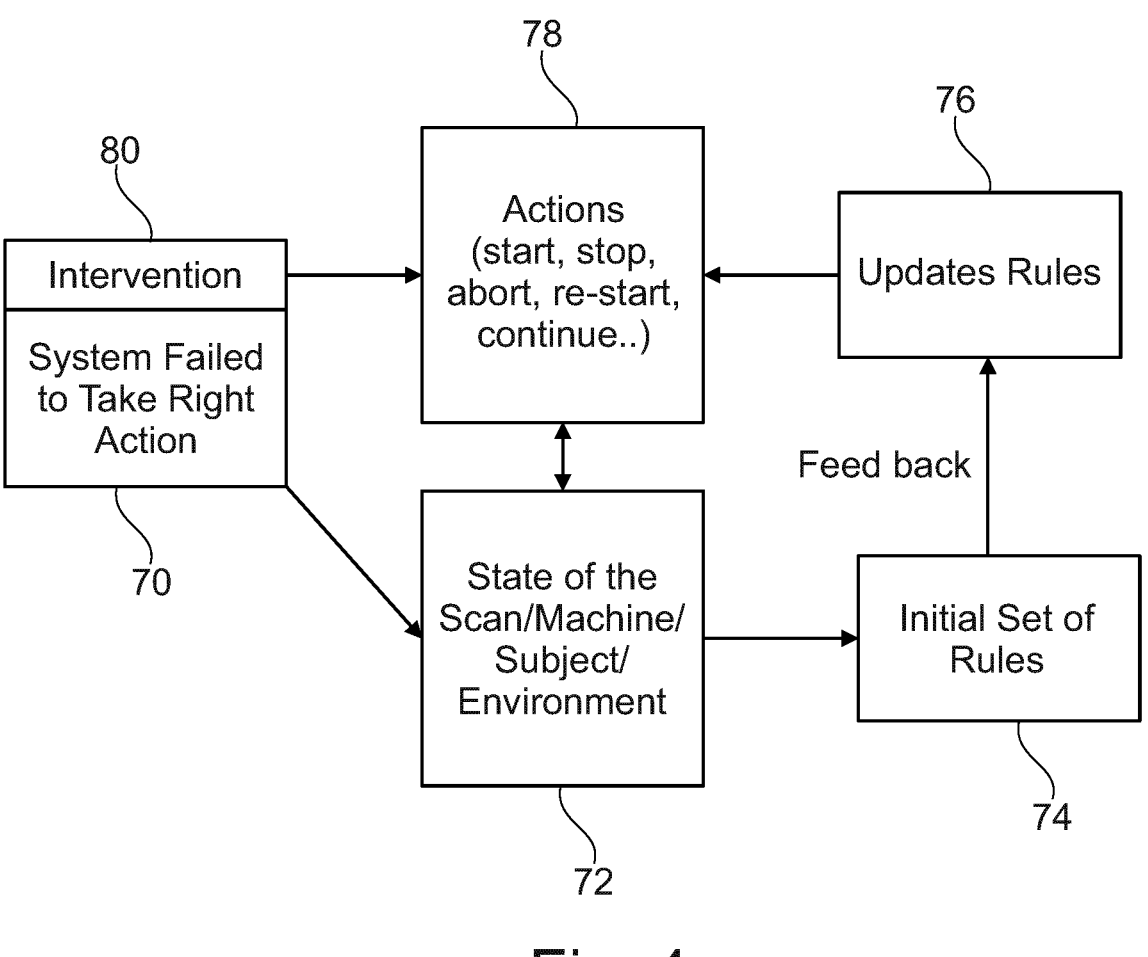
FIG. 4 shows an exemplary active learning mechanism.

FIG. 4 shows an exemplary active learning mechanism. In this example, if the system fails to take the right action (block 70), the states of the scan, machine, patient, and environment captured during the scan (block 72) are provided as a feedback to update the initial set of rules (block 74). The updated rules (block 76) are then used as new rules for the system to output states (block 78) like "start", "stop", "abort", "re-start", "continue", etc. Additionally, since the system fails to take the right action (block 70), a user intervention (block 80) may be needed to e.g. stop or abort the scan procedure. The scan procedure may be re-started after the rules have been updated.

Figure 5:
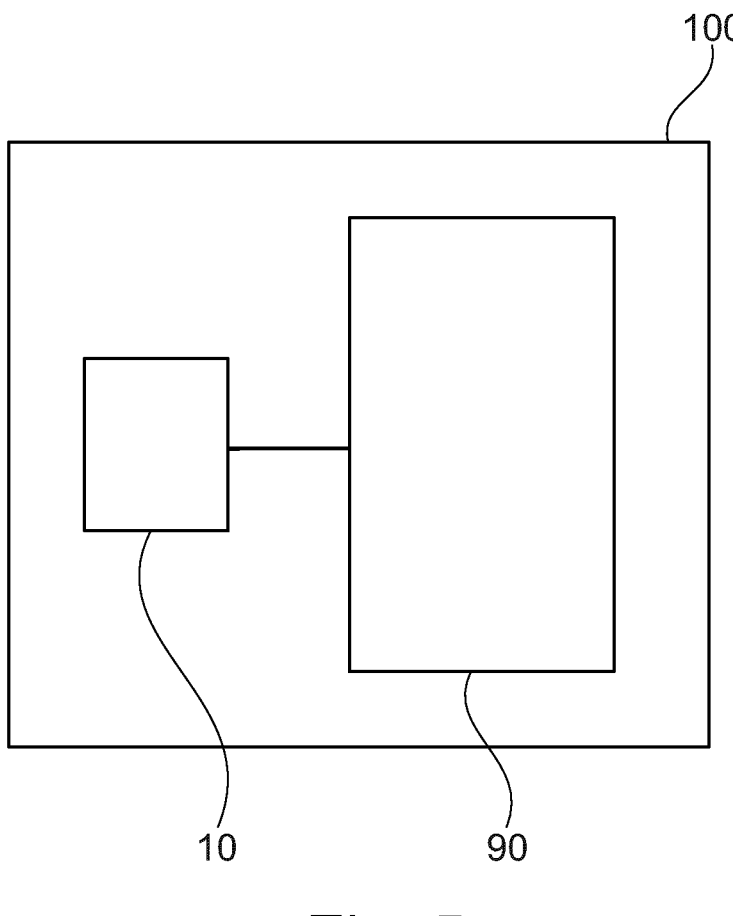
FIG. 5 shows an exemplary autonomous imaging system.

FIG. 5 shows an exemplary autonomous imaging system 100, which comprises an autonomous imaging apparatus 90 and a rule engine apparatus 10 as described above. The autonomous imaging apparatus 90 is configured to acquire an image of a patient based on a determined action provided by the rule engine apparatus 10.

Examples of the autonomous imaging apparatus 90 may include, but are not limited to, x-ray imaging apparatus, magnetic resonance imaging apparatus, computerized tomography scanner, positron emission tomography scanner, and the like.

In the example of FIG. 5, the rule engine apparatus 10 is a separate device configured to communicate with the autonomous imaging apparatus 90 through a wireless and/or a wire-based interface. However, in alternative examples, the rule engine apparatus 10 may resident in the autonomous imaging apparatus 90 e.g. running as software routines.

Figure 6:
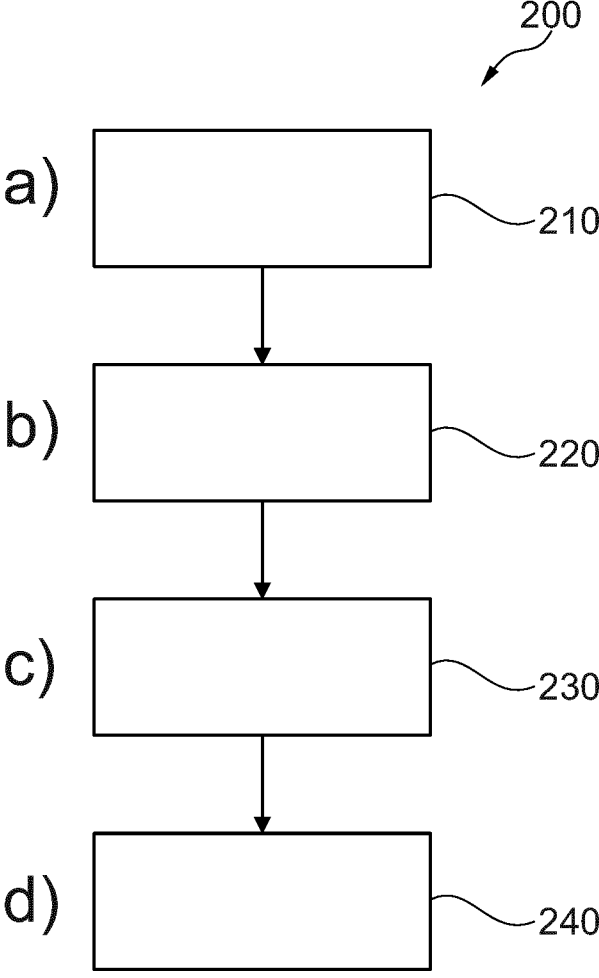
FIG. 6 shows a flow chart of a method for evaluating an autonomous scan procedure for controlling an autonomous imaging apparatus to acquire an image of a patient.

FIG. 6 shows a flow chart of a method 200 for evaluating an autonomous scan procedure for controlling an autonomous imaging apparatus to acquire an image of a patient. The method may be carried out by the exemplary apparatus shown in FIG. 1.

In step 210, i.e. step a), a data input indicative of an event in an autonomous image acquisition workflow is received e.g. via an input unit of the exemplary apparatus 10.

As discussed in detail hereinbefore, the data input may comprise data collected from the patient, data collected from a device and the autonomous imaging apparatus, data collected from an imaging room, and/or data collected from a user input. These data input may be used to evaluate the suitability of patient for autonomous scan, subsequent preparations, prevention of injury, subjective human intervention, etc.

In step 220, i.e. step b), a master engine unit selects, for the data input, one or more workflow step rule engine units from a plurality of workflow step rule engine units to determine a set of readiness indices. Each workflow step rule engine unit is associated with a respective set of rules. Each of the one or more selected workflow step rule engine units is configured to execute, in response to the data input, one or more rules of the respective rule set to generate a respective readiness index indicative of a state of being prepared for a particular step in the autonomous image acquisition workflow. For example, in the patient preparation phase, the master rule engine may select one or more workflow step rule engine units that are associated with patient preparation to determine a set of readiness indices.

In some examples, each rule may correspond to a specific workflow step in the autonomous image acquisition workflow, and workflow steps between different rules may be different. The master rule engine unit is configured to associate the data input to at least one of the one or more selected workflow step rule engine units with a sub-step of the specific workflow step. For example, in the patient preparation phase, multiple workflow step rule engine units may be used to provide different readiness indices, such as "anxiety index", "sedation index", "contrast material index", "metal object risk index", and "patient condition risk index". These workflow steps may also be referred to as sub-steps of the patient preparation workflow step.

In step 230, i.e. step c), the master engine unit then determines an action of the autonomous imaging apparatus based on the set of readiness indices. The determined action may comprise one or more of starting image acquisition, aborting image acquisition, and stopping image acquisition.

For determining the action of starting image acquisition, the master rule engine unit is configured to select, for the data input, one or more workflow step rule engine units from the plurality of workflow step rule engine units to determine a set of readiness indices about a device indicative a state of the autonomous imaging apparatus being prepared for starting image acquisition and a set of readiness indices about the patient indicative a state of the patient being prepared for starting image acquisition.

For determining the action of aborting image acquisition, the master rule engine unit is configured to select, for the data input, one or more workflow step rule engine units from the plurality of workflow step rule engine units to determine a set of readiness indices about a device indicative a state of the autonomous imaging apparatus not being suitable for continuing image acquisition and/or a set of readiness indices about the patient indicative a state of the patient not being suitable for continuing image acquisition.

For determining the action of stopping image acquisition, the master rule engine unit is configured to select, for the data input, one or more workflow step rule engine units from the plurality of workflow step rule engine units to determine a set of readiness indices indicative of one or more of the following: planned end, scan protocol completed, image quality assessment, coverage of organ of interest, and stable internet access by remote operator.

In step 240, i.e. step d), an output unit of the exemplary apparatus 10 outputs the determined action, which is usable for controlling the autonomous imaging apparatus.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A system comprising:
   an input unit;
   a master rule engine unit;
   a plurality of workflow step rule engine units, each workflow step rule engine unit being associated with a respective set of rules; and
   an output unit;
   wherein the input unit is configured to receive a data input indicative of an event in an autonomous image acquisition workflow and a plurality of sets of workflow steps, each having a plurality of segments, that define phases within the autonomous image acquisition workflow for the event, wherein the data input indicative of an event is received from a pre-trained machine learning algorithm that outputs the event based on a determined probability indicating whether the event is likely to happen;

wherein the master rule engine unit is configured to select, for the data input, one or more workflow step rule engine units from the plurality of workflow step rule engine units to determine a set of readiness indices of an autonomous imaging apparatus, each of the one or more workflow step rule engine units defining rules for a specific segment of the autonomous image acquisition workflow, wherein each of the one or more selected workflow step rule engine units is configured to execute, in response to the data input, one or more rules of the respective rule set to generate a respective readiness index indicative of a state of being prepared for a particular workflow step in the autonomous image acquisition workflow;

wherein each rule corresponds to a specific workflow step in the autonomous image acquisition workflow, and workflow steps between different rules are different;

wherein the master rule engine unit is further configured to determine an action of the autonomous imaging apparatus based on the set of readiness indices; and wherein the master rule engine unit is further configured to control, via the output unit, the autonomous imaging apparatus to perform the determined action in acquiring an image of a patient.

2. The system of claim 1, wherein the master rule engine unit is configured to associate the data input to at least one of the one or more selected workflow step rule engine units with a sub-step of the specific workflow step.

3. The system of claim 1, wherein the plurality of workflow step rule engine units are configured to use an active learning mechanism to update respective rule sets.

4. The system of claim 1, wherein the data input comprises at least one:

data collected from the patient;

data collected from a device used in the autonomous scan procedure;

data collected from the autonomous imaging apparatus;

data collected from an imaging room; or data collected from a user input.

5. The system of claim 4, wherein the data collected from the patient comprises at least one of:

sensor data collected from sensors for monitoring the patient;

clinical data of the patient; or patient profile data.

6. The system of claim 1, wherein the determined action comprises at least one of:

starting image acquisition;

aborting image acquisition; or stopping image acquisition as planned.

7. The system of claim 6, wherein for determining the action of starting image acquisition, the master rule engine unit is configured to select, for the data input, one or more workflow step rule engine units from the plurality of workflow step rule engine units to determine a set of readiness indices about a device indicative a state of the autonomous imaging apparatus being prepared for starting image acquisition and a set of readiness indices about the patient indicative a state of the patient being prepared for starting image acquisition.

8. The system of claim 6, wherein for determining the action of aborting image acquisition, the master rule engine unit is configured to select, for the data input, one or more workflow step rule engine units from the plurality of workflow step rule engine units to determine a set of readiness indices about a device indicative a state of the autonomous imaging apparatus not being suitable for continuing image acquisition and/or a set of readiness indices about the patient indicative a state of the patient not being suitable for continuing image acquisition.

9. The system of claim 6, wherein for determining the action of stopping image acquisition, the master rule engine unit is configured to select, for the data input, one or more workflow step rule engine units from the plurality of workflow step rule engine units to determine a set of readiness indices indicative of at least one or more of the following:

planned end;

scan protocol completed;

image quality assessment;

coverage of organ of interest; or stable internet access by remote operator.

10. A method, where each of the steps of the method are implemented by one or more processors for evaluating an autonomous scan procedure for controlling an autonomous imaging apparatus to acquire an image of a patient, the method comprising:

a) receiving a data input indicative of an event in an autonomous image acquisition workflow and a plurality of sets of workflow steps, each having a plurality of segments, that define phases within the autonomous image acquisition workflow for the event, wherein the data input indicative of an event is received from a pre-trained machine learning algorithm that outputs the event based on a determined probability indicating whether the event is likely to happen;

b) selecting for the data input, one or more workflow step rule engine units from a plurality of workflow step rule engine units to determine a set of readiness indices of the autonomous imaging apparatus, each of the one or more workflow step rule engine units defining rules for a specific segment of the autonomous image acquisition workflow, wherein each workflow step rule engine unit is associated with a respective set of rules;

wherein each rule corresponds to a specific workflow step in the autonomous image acquisition workflow, and workflow steps between different rules are different; and wherein each of the one or more selected workflow step rule engine units is configured to execute, in response to the data input, one or more rules of the respective rule set to generate a respective readiness index indicative of a state of being prepared for a particular step in the autonomous image acquisition workflow;

c) determining an action of the autonomous imaging apparatus based on the set of readiness indices; and d) controlling, by the one or more processors, the autonomous imaging apparatus to perform the determined action when acquiring the image of the patient.

11. A non-transitory computer readable medium which, when executed by the one or more processors, causes the one or more processors to perform the method according to claim 10.

12. A system comprising:

at least one processor; and a non-transitory memory storing instructions that, when executed by the at least one processor, cause the at least one processor to;

receive a data input indicative of an event in an autonomous image acquisition workflow and a plurality of sets of workflow steps, each having a plurality of segments, that define phases within the autonomous image acquisition workflow for the event, wherein the data input indicative of an event is received from a pre-trained machine learning algorithm that outputs the event based on a determined probability indicating whether the event is likely to happen;

select, for the data input, one or more workflow step rule engines from a plurality of workflow step rule engines to determine a set of readiness indices of the autonomous imaging apparatus, each of the one or more workflow step rule engine units defining rules for a specific segment of the autonomous image acquisition workflow, wherein each workflow step rule engine is associated with a respective set of rules, wherein each of the one or more selected workflow step rule engines is configured to execute, in response to the data input, one or more rules of the respective set of rules to generate a respective readiness index indicative of a state of being prepared for a particular step in the autonomous image acquisition workflow, and wherein each rule corresponds to a specific workflow step in the autonomous image acquisition workflow, and workflow steps between different rules are different;

determine an action of the autonomous imaging apparatus based on the set of readiness indices; and output the determined action to the autonomous imaging apparatus and control the autonomous imaging apparatus to perform the determined action in acquiring an image of a patient.

13. The system of claim 12, wherein the instructions further cause the at least one processor to associate the data input to at least one of the one or more selected workflow step rule engines with a sub-step of the specific workflow step.

14. The system of claim 12, wherein the determined action comprises at least one of:

starting image acquisition;

aborting image acquisition; or stopping image acquisition as planned.

15. The system of claim 14, wherein for determining the action of starting image acquisition, the instructions further cause the at least one processor to select, for the data input, one or more workflow step rule engines from the plurality of workflow step rule engines to determine a set of readiness indices about a device indicative a state of the autonomous imaging apparatus being prepared for starting image acquisition and a set of readiness indices about the patient indicative a state of the patient being prepared for starting image acquisition.

16. The system of claim 14, wherein for determining the action of aborting image acquisition, the instructions further cause the at least one processor to select, for the data input, one or more workflow step rule engines from the plurality of workflow step rule engines to determine a set of readiness indices about a device indicative a state of the autonomous imaging apparatus not being suitable for continuing image acquisition and/or a set of readiness indices about the patient indicative a state of the patient not being suitable for continuing image acquisition.

17. The system of claim 14, wherein for determining the action of stopping image acquisition, the instructions further cause the at least one processor to select, for the data input, one or more workflow step rule engines from the plurality of workflow step rule engines to determine a set of readiness indices indicative of at least one or more of:

planned end;

scan protocol completed;

image quality assessment;

coverage of organ of interest; or stable internet access by remote operator.

* * * * *